United States Patent
Karle et al.

(10) Patent No.: US 9,095,544 B2
(45) Date of Patent: Aug. 4, 2015

(54) OTIC COMPOSITION FOR COMPANION ANIMALS

(75) Inventors: Joachim Karle, Ruesselsheim (DE); Reinhard Seffner, Basdahl (DE); Horst Sollinger, Raubling (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 13/995,828

(22) PCT Filed: Dec. 21, 2011

(86) PCT No.: PCT/EP2011/073667
§ 371 (c)(1),
(2), (4) Date: Sep. 5, 2013

(87) PCT Pub. No.: WO2012/085139
PCT Pub. Date: Jun. 28, 2012

(65) Prior Publication Data
US 2014/0228444 A1     Aug. 14, 2014

(30) Foreign Application Priority Data
Dec. 23, 2010 (EP) .................................. 10196910

(51) Int. Cl.
| | | |
|---|---|---|
| A61K 31/14 | (2006.01) | |
| C07C 211/62 | (2006.01) | |
| A61K 8/34 | (2006.01) | |
| A61K 8/41 | (2006.01) | |
| A61Q 19/10 | (2006.01) | |
| A61K 9/00 | (2006.01) | |
| A61K 47/10 | (2006.01) | |
| A61K 47/20 | (2006.01) | |

(52) U.S. Cl.
CPC ................. *A61K 31/14* (2013.01); *A61K 8/345* (2013.01); *A61K 8/416* (2013.01); *A61K 9/0046* (2013.01); *A61K 47/10* (2013.01); *A61K 47/20* (2013.01); *A61Q 19/10* (2013.01)

(58) Field of Classification Search
CPC ........ A61K 31/14; A61K 8/345; A61K 8/416; A61K 9/0046; A61K 47/10
USPC .................................. 514/642; 564/291, 295
See application file for complete search history.

(56) References Cited

U.S. PATENT DOCUMENTS

2006/0269485 A1* 11/2006 Friedman et al. ............... 424/45
2008/0166436 A1    7/2008 Pusillo
2009/0111780 A1*  4/2009 Giordano ..................... 514/171

FOREIGN PATENT DOCUMENTS

| WO | 2008020769 A1 | 2/2008 |
| WO | 2009052566 A1 | 4/2009 |
| WO | 2010109422 A1 | 9/2010 |
| WO | 2012085139 A1 | 6/2012 |

OTHER PUBLICATIONS

Cabenda et al. "Serous otitis media (S.O.M.). A bacteriological study of the ear canal and the middle ear". International Journal of Pediatric Otorhinolaryngology, vol. 16, 1988, pp. 119-124.
International Search Report and Written Opinion for PCT/EP2011/073667 mailed Feb. 15, 2012.
Little, Chris, "Medical treatment of otitis externa in the dog and cat". In Practice, vol. 18, No. 2, 1996, pp. 66-69, 71.

* cited by examiner

*Primary Examiner* — My-Chau T Tran
(74) *Attorney, Agent, or Firm* — Michael P. Morris; Joyce L. Morrison

(57) ABSTRACT

The invention relates to a composition containing cetrimide suitable for cleaning inflamed or non-inflamed ears of animals, preferably of companion animals such as dogs and cats. The composition further comprises one or more carriers, such as for example wetting agents and humectants.

37 Claims, No Drawings

OTIC COMPOSITION FOR COMPANION ANIMALS

FIELD OF THE INVENTION

The present invention is directed to a new otic composition for the use in an animal as for example a companion animals, particularly for dogs and cats.

BACKGROUND OF THE INVENTION

The field of the invention is that of compositions for the use as a cleaning agent of ears of an animal, preferably companion animals such as dogs and cats.

Dogs show signs of ear problems when starting to shake his head suddenly. The reason can be amongst others a foreign body, such as for example a grass seed, in the pet's ear. Other foreign organisms such as tiny ear mites can also produce irritation and wax.

Sometimes ear disease is straightforward and easily treated, when caused by a foreign body for example, but many ear problems are recurrent. The ear canal may be very narrow or is lined with plenty of hairs inside so that wax gets trapped. Skin that lines the ears can also give rise to problems such as allergies. The result is excess wax production, inflammation, infection and pain.

Thus, regular ear cleaning is vital, especially also as the vigorous head shaking can result in breaking blood vessels in the earflap, which bleeds and forms a blood blister (haematoma).

Typical signs in cats that suffer of an ear disease include unusual odour, scratching or rubbing of ears and head, discharge in the ears, redness or swelling of the ear canal, shaking of the head or tilting it to one side, pain around the ears, and changes in behaviour such as depression or irritability. Ear disease is a common condition in cats.

Inflammation of the outer ear canal is otitis externa. Primary causes of otitis externa include parasites such as ear mites (very common in cats) or foreign bodies. Probably the most common primary cause of otitis externa is allergies, which can be either to inhaled substances (atopy) or food.

Perpetuating factors such as bacterial and fungal infections of the outer ear can increase the severity of the condition and play a major role in chronic or recurrent otitis externa. Otitis media, which is inflammation/infection of the middle ear, is often a source of constant re-infection of the outer ear. One of the most significant perpetuating factors is ear canal hypertrophy (thickening), which may progress into a complete closure of the outer ear canal and make medical treatment of the ear almost impossible.

Treatment of otitis externa has to be according to the underlying, predisposing and perpetuating factors that are present. Treatment options include ear cleaning or flushing, ear medications for infections and steroids to reduce inflammation.

Animals with atopy (inhalant allergy) and food allergies are unlikely to be cured and may require continual ear care to minimize flare ups of otitis externa.

Proper ear cleaning is an important factor as ear medication applied on top of earwax or pus is ineffective and may become inactivated. The ear cleaning agent should be mildly antiseptic, dissolve earwax and coat the ear canal to provide long lasting action.

Known products for this purpose make use of chlorhexidine in general as active principle, but its effectiveness depends strongly on concentration. When chlorhexidine is used at high concentrations, it can result in undesired collateral effects. Other known active principles are iodine compounds that have a wide spectrum of antiinfectives against bacteria, fungi, spores, protozoa, viruses, and yeasts. Aqueous iodine is less effective than alcoholic solutions, but alcoholic component is drying and irritating to abrased skin. Povidone iodine is convenient to use as it is less irritating, but not as effective.

The aim of the invention is to provide a new composition for companion animals, in particular for dogs and cats that can be used to clean healthy or inflamed ears more effectively. It is desired to use an active ingredient that is more effective at low concentrations as well as more tolerable compared to other otic compositions. The composition exhibits the properties of cleaning, maintaining/nursing and disinfecting ears of companion animals, especially of dogs and/or cats. Furthermore, the usage of this composition is animal and user friendly.

DESCRIPTION OF THE INVENTION

The present invention relates to a composition comprising cetrimide suitable for cleaning ears of an animal. The animal to be treated is a companion animal such as but not limited to dogs and cats. The composition comprising cetrimide is also suitable for cleaning inflamed ears of an animal, preferably a companion animal such as a dog or a cat.

The antibacterial agent cetrimide is preferably employed in a concentration range that has no ototoxic effect. Cetrimide has not been used in a veterinary context before. Cetrimide operates by attacking and disrupting cell walls of germs such as but not limited to bacteria, viruses, fungi, and protozoa that hereby are agonized. Thus, the composition comprises cetrimide as the active ingredient preferably in a concentration range from about 0.1 to 0.5% by weight (wt %), preferably 0.1 to 0.4 wt %, more preferably 0.1 to 0.3 wt %, even more preferred 0.1 to 0.2 wt %, most preferred are 0.15 wt % or 0.154 wt %. Thus, according to a further aspect, a composition is provided which comprises about 0.1 to 0.5 wt % of cetrimide preferably 0.1 to 0.4 wt %, more preferably 0.1 to 0.3 wt %, even more preferred 0.1 to 0.2 wt %, most preferred is 0.15 wt % which composition is suitable for cleaning ears of an animal.

Cetrimide is a complex compound that contains cetrimonium cation and various anions. In aqueous solutions cetrimide dissociates into a large complex cation, namely the cetrimonium cation, responsible for the activity and a smaller inactive anion. The cetrimonium cation, which is also named hexadecyltrimethyl ammonium, is an effective antiseptic agent against bacteria and fungi and therefore the use of cetrimonium cation is preferred. Furthermore, it is a cationic surfactant. Cetrimide used in the composition is present in the form of its cation with one or more anions, hence cetrimide comprises for example cetrimonium bromide (synonyms include cetyltrimethyl ammonium bromide and hexadecyltrimethyl ammonium bromide), tetradecyltrimethyl ammonium bromide, dodecyltrimethyl ammonium bromide, cetrimonium chloride or cetrimonium stearate. According to a further aspect of the invention, a composition is provided which comprises cetrimide comprising cetrimonium bromide, cetrimonium chloride and cetrimonium stearate, tetradecyltrimethyl ammonium bromide, dodecyltrimethyl ammonium bromide or mixtures thereof. Preferably, cetrimide contained within the composition according to the invention is selected from the group consisting of cetrimonium bromide, cetrimonium chloride and cetrimonium stearate, tetradecyltrimethyl ammonium bromide, dodecyltrimethyl ammonium bromide or mixtures thereof, more preferred is tetradecyltrimethyl ammonium bromide, cetrimonium bromide, dodecyltrimethyl ammonium bromide or mixtures thereof, even more preferred is cetrimonium bromide. Furthermore, the composition according to the invention comprises cetrimide in a concentration of about 0.1 to 0.5 wt %, preferably 0.1 to 0.4 wt %, more preferably 0.1 to 0.3 wt %, even more preferred 0.1 to 0.2 wt %, most preferred are 0.15 wt % or 0.154 wt %.

A composition suitable for cleaning ears of animals is provided, which comprises cetrimide or preferably the cetrimide cation with one or more anions and one or more carriers. Thus, the composition comprises one or more carriers, which is selected from the group consisting of one or more wetting agents, one or more humectants, or one or more humectants and one or more wetting agent. According to a further aspect of the invention the composition comprises cetrimide as defined above, a wetting agent and/or a humectant. Thus, the composition according to the invention contains one or more cetrimide compounds selected from the group consisting of cetrimonium bromide (synonyms include cetyltrimethyl ammonium bromide and hexadecyltrimethyl ammonium bromide), tetradecyltrimethyl ammonium bromide, dodecyltrimethyl ammonium bromide, cetrimonium chloride and cetrimonium stearate, and further one or more wetting agent and/or humectant. The concentration of cetrimide in the composition is preferably as defined above.

The wetting agent of the cetrimide composition is selected from the group consisting of propylene glycol, 1,3-butandiol, ethanol, docusate sodium and dimethyl sulfoxide (DMSO), preferably propylene glycol, docusate sodium or dimethyl sulfoxide, even more preferred is propylene glycol. The concentration of the wetting agent ranges from 5 to 20 wt %, preferably 5 to 15 wt %, more preferred 8 to 12 wt %, even more preferred 10 wt %. Thus, according to a another aspect, a cetrimide composition is provided, which comprises a wetting agent selected from the group consisting of propylene glycol, 1,3-butandiol, ethanol, docusate sodium and dimethyl sulfoxide (DMSO), preferably propylene glycol with a concentration of 5 to 20 wt %, preferably 5 to 15 wt %, more preferred 8 to 12 wt %, even more preferred 10 wt %. According to another aspect, the cetrimide composition of the invention contains preferably polypropylene glycol as a wetting agent in a concentration at 10 wt %. Furthermore, propylene glycol also acts as a surfactant that penetrates and hereby softens any dirt within the ear. This process enables an easier removal of any earwax or similar dirt within the ear. Additionally, polypropylene glycol also has antibacterial properties since it also attacks cell walls of micro-organisms.

The humectant of the cetrimide composition is selected from the group consisting of glycerol, polyethylene glycol 200 or 400, peanut oil, almond oil, olive oil and sesame oil, preferably glycerol, polyethylene glycol 200 or 400, even more preferred glycerol. According to a further aspect, the cetrimide composition contains one or more of the above defined humectants. The concentration of the humectant in the cetrimide containing composition ranges from 5 to 20 wt %, preferably 5 to 15 wt %, more preferred 8 to 12 wt %, even more preferred 10 wt %. Thus, according to a further aspect of the invention, the cetrimide composition comprises a humectant selected from the group consisting of glycerol, polyethylene glycol 200 or 400, peanut oil, almond oil, olive oil and sesame oil, preferably glycerol, polyethylene glycol 200 or 400, even more preferred glycerol in a concentration range from 5 to 20 wt %, preferably 5 to 15 wt %, more preferred 8 to 12 wt %, even more preferred 10 wt %. Preferably, the cetrimide composition according to the invention comprises glycerol with a concentration at 10 wt %.

The cetrimide composition as described above has a pH in the range of pH 4-9, preferably from pH 5-8, most preferred is pH 7. Thus, according to a further aspect, the composition according to the invention, which comprises cetrimide as defined above and one or more wetting agents and/or one or more humectants, is provided with a pH of 4-9, preferably pH 5-8, even more preferred pH 7. Preferably, the cetrimide composition according to the invention has a pH of 7. Thus according to another aspect of the invention, the cetrimide composition comprises cetrimide, glycerol and polypropylene glycol with a pH of 7. Preferably, an acidifying or alkalizing agent is used in order to reach the desired pH.

According to a further aspect, the cetrimide composition according to the invention contains for example 10 wt % propylene glycol, 0.16 wt % cetrimide, a glycerol concentration selected from the group consisting of 5 to 20 wt %, 5 to 15 wt %, preferably 10 wt % and purified water added in an amount to reach the total weight of the composition of 100 wt %; or for example 10 wt % glycerol, 0.16 wt % cetrimide, a propylene glycol concentration selected from the group consisting of 5 to 20 wt %, 5 to 15 wt %, preferably 10 wt % and purified water added in an amount to reach the total weight of the composition of 100 wt %; or for example 10 wt % glycerol, 10 wt % propylene glycol, a cetrimide concentration selected from the group consisting of 0.1 to 0.5 wt %, preferably 0.1 to 0.4 wt %, more preferably 0.1 to 0.3 wt %, even more preferred 0.1 to 0.2 wt %, most preferred is 0.15 wt %, and purified water added in an amount to reach the total weight of the composition of 100 wt %; or mixtures thereof. Furthermore, the composition according to the invention comprises preferably 10 wt % propylene glycol, 10 wt % glycerol, 0.15 wt % cetrimide and 79.95 wt % purified water. The composition according to the invention preferably comprises 10 wt % propylene glycol, 10 wt % glycerol, 0.154 wt % cetrimide and 79.846 wt % purified water.

Further examples for the cetrimide composition are as follows, but not limited to: 10 wt % propylene glycol, 10 wt % glycerol, 0.15 wt % cetrimide and 79.95 wt % purified water; or 15 wt % propylene glycol, 10 wt % glycerol, 0.15 wt % cetrimide and 74.85 wt % purified water; or 20 wt % propylene glycol, 10 wt % glycerol, 0.15 wt % cetrimide and 69.85 wt % purified water; or 10 wt % propylene glycol, 20 wt % glycerol, 0.15 wt % cetrimide and 69.85 wt % purified water; or 20 wt % propylene glycol, 20 wt % glycerol, 0.15 wt % cetrimide and 59.85 wt % purified water; or 15 wt % propylene glycol, 15 wt % glycerol, 0.15 wt % cetrimide and 69.85 wt % purified water; or 5 wt % propylene glycol, 5 wt % glycerol, 0.15 wt % cetrimide and 89.85 wt % purified water; or 5 wt % propylene glycol, 10 wt % glycerol, 0.15 wt % cetrimide and 84.85 wt % purified water; or 10 wt % propylene glycol, 5 wt % glycerol, 0.15 wt % cetrimide and 84.85 wt % purified water; or 10 wt % propylene glycol, 10 wt % glycerol, 0.1 wt % cetrimide and 79.99 wt % purified water; or 15 wt % propylene glycol, 15 wt % glycerol, 0.1 wt % cetrimide and 69.95 wt % purified water; or 20 wt % propylene glycol, 20 wt % glycerol, 0.1 wt % cetrimide and 59.9 wt % purified water; or 10 wt % propylene glycol, 10 wt % glycerol, 0.2 wt % cetrimide and 79.8 wt % purified water; or 15 wt % propylene glycol, 10 wt % glycerol, 0.2 wt % cetrimide and 74.8 wt % purified water; or 15 wt % propylene glycol, 15 wt % glycerol, 0.2 wt % cetrimide and 69.8 wt % purified water; or 20 wt % propylene glycol, 15 wt % glycerol, 0.2 wt % cetrimide and 64.8 wt % purified water; or 15 wt % propylene glycol, 20 wt % glycerol, 0.2 wt % cetrimide and 64.8 wt % purified water; or 20 wt % propylene glycol, 20 wt % glycerol, 0.2 wt % cetrimide and 59.9 wt % purified water.

In a further aspect of the invention, said examples for the cetrimide composition as described above are combined with antiparasitic compounds that attack for examples mites or ticks. The antiparasitic compound can be but is not limited to simethicone, which is a mixture of polydimethylsiloxane and silica gel.

The above defined cetrimide composition, which contains cetrimide preferably in combination with one or more wetting agents or one or more humectants, or one or more wetting agents and one or more humectants is very effective and has not been employed within veterinary science before. The composition is a disinfecting composition that dissolves undesired dirt and/or earwax within the ear of an animal, preferably a companion animal such as a dog or cat. Furthermore, the composition has antibacterial properties that are achieved through all three components, whereof one has additional moisturising properties. The preferred pH of 7.0 ensures that all of the components of the composition will be used under optimal conditions to be effective on the environment of the skin. This is one of the advantages of the composition as it therefore does not irritate the skin of the animal. Another advantage of the composition is that it has no odor or smell in any way and therefore does not irritate the sensitive noses of an animal as for example companion animals, especially of dogs and cats.

The cetrimide composition as described above is used for cleaning ears of a companion animal. Furthermore, the cetrimide composition is suitable for the use of cleaning inflamed ears of a companion animal. The companion animal which ears are cleaned, or which infected ears are cleaned with the cetrimide composition of the invention prior to treatment is a dog or cat.

Administration of the above described composition is between 1 to 7 times a day, preferably 2 to 6, even more preferred 3 to 5 times per day. The amount to be used of the composition in each cleaning procedure/application is 1 to 50 ml. Thus the ears of an animal, preferably a companion animal, even more preferred a dog or cat, are cleaned 1 to 7 times a day, preferably 2 to 6, even more preferred 3 to 5 times per day with an amount of the composition according to the invention of 1-50 ml per application.

The cetrimide composition is being used for the exterior part of the ear only. Thus, according to a further aspect, provided is a process of cleaning ears, preferably the exterior ear of an animal, preferably of a cat or a dog, by using a cetrimide composition. Preferably, the cetrimide composition is any one of the cetrimide compositions described herein. The process of using the composition for cleaning the exterior ear of an animal comprising the steps: a) pouring the composition, as defined above, into the auditory canal of the animal; b) let the composition react within the auditory canal of the animal; c) removing the composition from the auditory canal of the animal. In said process the ear is preferably massaged while the composition reacts. In the described method 1 to 50 ml are preferably used in step a). Furthermore, the process or more specifically the process steps a) to c) are repeated according to a further aspect.

In another aspect of the invention the process of using the composition for cleaning the exterior ears of an animal, preferably a companion animal such as a dog or cat, comprises the following steps: a) the cetrimide composition is poured into the auditory canal; b) then the ear is massaged for 1 to 2 minutes to favour the exit of the composition mixed with earwax; c) the composition mixed with earwax will be removed, carefully cleaned and dried with cleaning appliances such as but not limited to any type of cotton or gauzes. The process steps a), b) and c) are repeated if one cleaning application was not sufficient due to the state of the ear. This cleaning process with the cetrimide composition helps keeping chronic or acute external otitis of an animal, preferably companion animals, even more preferred dogs or cats, under control.

The cetrimide composition is poured into the ears either with a syringe, cannula or directly from the bottle. The bottle contains a volume of the composition of 25 to 500 ml, 50 to 400 ml, 50 to 300 ml, 50 to 200 ml or 100 ml, preferably 100 ml.

The cleaning appliances are defined as medical cleaning instruments such as for example cotton swabs, cotton buds, medical gauzes, cotton wool pads, sponges, clothes/tissue or wipes, preferably cotton swabs and medical gauzes.

The cetrimide composition as described above as well as its application contributes to the prevention of otic pathologies and diseases such as otitis externa. It further contributes to alleviation of already inflamed ears. Thus, said cetrimide composition is for cleaning ears of an animal, preferably a companion animal such as a dog or cat and said composition is also useful for preventing otic diseases such as otitis externa that is caused by for example parasites such as ear mites, allergies, other foreign bodies.

According to another aspect the cetrimide composition is for the use of preventing and/or treatment of otic diseases in animals, preferably a companion animal such as a dog or a cat. Preferably the cetrimide composition is for the use of preventing and/or treatment of otitis externa in animals, preferably a companion animal such as a dog or a cat.

EXAMPLES

The following examples serve to further illustrate the present invention; but the same should not be construed as a limitation of the scope of the invention disclosed herein.

| Material | Weight per 100 g | Weight per 100 g | Weight per 100 g |
| --- | --- | --- | --- |
| Cetrimide | 0.10 | 0.154 | 0.4 |
| Propylene glycol | 10 | 10 | 10 |
| Glycerol 85% (w/v) | 10 | 10 | 10 |
| Water for injection | 79.9 | 79.846 | 79.6 |

| Material | Weight per 100 g | Weight per 100 g | Weight per 100 g |
| --- | --- | --- | --- |
| Cetrimide | 0.10 | 0.154 | 0.4 |
| Propylene glycol | 5 | 5 | 5 |
| Glycerol 85% (w/v) | 10 | 10 | 10 |
| Water for injection | 84.9 | 84.846 | 84.6 |

| Material | Weight per 100 g | Weight per 100 g | Weight per 100 g |
| --- | --- | --- | --- |
| Cetrimide | 0.10 | 0.154 | 0.4 |
| Propylene glycol | 20 | 20 | 20 |
| Glycerol 85% (w/v) | 10 | 10 | 10 |
| Water for injection | 69.9 | 69.846 | 69.6 |

| Material | Weight per 100 g | Weight per 100 g | Weight per 100 g |
| --- | --- | --- | --- |
| Cetrimide | 0.10 | 0.154 | 0.4 |
| Propylene glycol | 10 | 10 | 10 |
| Glycerol 85% (w/v) | 5 | 5 | 5 |
| Water for injection | 84.9 | 84.846 | 84.6 |

-continued

| Material | Weight per 100 g | Weight per 100 g | Weight per 100 g |
|---|---|---|---|
| Cetrimide | 0.10 | 0.154 | 0.4 |
| Propylene glycol | 10 | 10 | 10 |
| Glycerol 85% (w/v) | 20 | 20 | 20 |
| Water for injection | 69.9 | 69.846 | 84.6 |

| Material | Weight per 100 g | Weight per 100 g | Weight per 100 g |
|---|---|---|---|
| Cetrimide | 0.10 | 0.154 | 0.4 |
| Propylene glycol | 10 | 10 | 10 |
| Polyethylene glycol 200 | 10 | 10 | 10 |
| Water for injection | 79.9 | 79.846 | 79.6 |

| Material | Weight per 100 g | Weight per 100 g | Weight per 100 g |
|---|---|---|---|
| Cetrimide | 0.10 | 0.154 | 0.4 |
| Propylene glycol | 5 | 5 | 5 |
| Polyethylene glycol 200 | 10 | 10 | 10 |
| Water for injection | 84.9 | 84.846 | 84.6 |

| Material | Weight per 100 g | Weight per 100 g | Weight per 100 g |
|---|---|---|---|
| Cetrimide | 0.10 | 0.154 | 0.4 |
| Propylene glycol | 20 | 20 | 20 |
| Polyethylene glycol 200 | 10 | 10 | 10 |
| Water for injection | 69.9 | 69.846 | 69.6 |

| Material | Weight per 100 g | Weight per 100 g | Weight per 100 g |
|---|---|---|---|
| Cetrimide | 0.10 | 0.154 | 0.4 |
| Propylene glycol | 10 | 10 | 10 |
| Polyethylene glycol 200 | 5 | 5 | 5 |
| Water for injection | 84.9 | 84.846 | 84.6 |

| Material | Weight per 100 g | Weight per 100 g | Weight per 100 g |
|---|---|---|---|
| Cetrimide | 0.10 | 0.154 | 0.4 |
| Propylene glycol | 10 | 10 | 10 |
| Polyethylene glycol 200 | 20 | 20 | 20 |
| Water for injection | 69.9 | 69.846 | 84.6 |

| Material | Weight per 100 g | Weight per 100 g | Weight per 100 g |
|---|---|---|---|
| Cetrimide | 0.10 | 0.154 | 0.4 |
| Dimethyl sulfoxide | 10 | 10 | 10 |
| Glycerol 85% (w/v) | 10 | 10 | 10 |
| Water for injection | 79.9 | 79.846 | 79.6 |

| Material | Weight per 100 g | Weight per 100 g | Weight per 100 g |
|---|---|---|---|
| Cetrimide | 0.10 | 0.154 | 0.4 |
| Dimethyl sulfoxide | 5 | 5 | 5 |
| Glycerol 85% (w/v) | 10 | 10 | 10 |
| Water for injection | 84.9 | 84.846 | 84.6 |

| Material | Weight per 100 g | Weight per 100 g | Weight per 100 g |
|---|---|---|---|
| Cetrimide | 0.10 | 0.154 | 0.4 |
| Dimethyl sulfoxide | 20 | 20 | 20 |
| Glycerol 85% (w/v) | 10 | 10 | 10 |
| Water for injection | 69.9 | 69.846 | 69.6 |

| Material | Weight per 100 g | Weight per 100 g | Weight per 100 g |
|---|---|---|---|
| Cetrimide | 0.10 | 0.154 | 0.4 |
| Dimethyl sulfoxide | 10 | 10 | 10 |
| Glycerol 85% (w/v) | 5 | 5 | 5 |
| Water for injection | 84.9 | 84.846 | 84.6 |

| Material | Weight per 100 g | Weight per 100 g | Weight per 100 g |
|---|---|---|---|
| Cetrimide | 0.10 | 0.154 | 0.4 |
| Dimethyl sulfoxide | 10 | 10 | 10 |
| Glycerol 85% (w/v) | 20 | 20 | 20 |
| Water for injection | 69.9 | 69.846 | 84.6 |

The invention claimed is:

1. A composition comprising cetrimide suitable for cleaning ears of animals, wherein the animal is a companion animal.

2. The composition according to claim 1, comprising cetrimide and one or more carriers.

3. The composition according claim 1, comprising cetrimide in a concentration range from 0.1 to 0.5 wt %.

4. The composition according to claim 2, wherein the carrier is at least one of a wetting agent and a humectant.

5. The composition according to claim 4, wherein the wetting agent is selected from the group consisting of propylene glycol, 1,3-butandiol, ethanol, docusate sodium and dimethyl sulfoxide (DMSO).

6. The composition according to claim 4, wherein the concentration range of the wetting agent is 5 to 20 wt %.

7. The composition according to claim 4, wherein the humectant is selected from the group consisting of glycerol, polyethylene glycol 200 or 400, peanut oil, almond oil, olive oil and sesame oil.

8. The composition according to claim 4, wherein the concentration range of the humectant is 5 to 20 wt %.

9. The composition according to claim 1, wherein the pH of said composition is in the range of pH 4 to 9.

10. The composition according to claim 1, wherein said companion animal is a dog or cat.

11. The composition according to claim 1, wherein said composition is used 3 to 5 times per day.

12. The composition according to claim 1, wherein the amount to be used in each application of said composition is 1 to 50 ml.

13. A composition comprising cetrimide suitable for cleaning inflamed ears of an animal, wherein the animal is a companion animal.

14. The composition according to claim 13, comprising cetrimide and one or more carriers.

15. The composition according claim 13 comprising cetrimide in a concentration range from 0.1 to 0.5 wt %.

16. The composition according to claim 14, wherein the carrier is at least one of a wetting agent and a humectant.

17. The composition according to claim 16, wherein the wetting agent is selected from the group consisting of propylene glycol, 1,3-butandiol, ethanol, docusate sodium and dimethyl sulfoxide (DMSO).

18. The composition according to claim 16, wherein the concentration range of the wetting agent is 5 to 20 wt %.

19. The composition according to claim 16, wherein the humectant is selected from the group consisting of glycerol, polyethylene glycol 200 or 400, peanut oil, almond oil, olive oil and sesame oil.

20. The composition according to claim 16, wherein the concentration range of the humectant is 5 to 20 wt %.

21. The composition according to claim 13, wherein the pH of said composition is in the range of pH 4 to 9.

22. The composition according to claim 13, wherein said companion animal is a dog or cat.

23. The composition according to claim 13, wherein said composition is used 3 to 5 times per day.

24. The composition according to claim 13, wherein the amount to be used in each application of said composition is 1 to 50 ml.

25. The composition according to claim 1, wherein the composition is suitable for the use of preventing otic diseases.

26. A process for cleaning the exterior ear of an animal comprising the steps: a) pouring the composition according to claim 1 into the auditory canal of the animal; b) let the composition react within the auditory canal of the animal; c) removing the composition from the auditory canal of the animal.

27. The process according to claim 26, wherein in that the ear is massaged while the composition reacts.

28. The process according to claim 26, wherein 1 to 50 ml are used in step a).

29. The process according to claim 26, wherein the process steps a) to c) are repeated.

30. A process for cleaning the exterior ear of an animal comprising the steps: a) pouring the composition according to claim 13 into the auditory canal of the animal; b) let the composition react within the auditory canal of the animal; c) removing the composition from the auditory canal of the animal.

31. The process according to claim 30, wherein in that the ear is massaged while the composition reacts.

32. The process according to claim 30, wherein 1 to 50 ml are used in step a).

33. The process according to claim 30, wherein the process steps a) to c) are repeated.

34. The composition according to claim 1, comprising cetrimide in a concentration of 0.15 wt %.

35. The composition according to claim 1, comprising cetrimide in a concentration of 0.154 wt %.

36. The composition according to claim 1, wherein the pH of said composition is pH 7.

37. A composition comprising cetrimide suitable for cleaning ears of animals, wherein the animal is a companion animal, the composition comprises cetrimide in a concentration range from 0.1 to 0.5 wt %, and a pH of the composition is in a range from pH 4 to pH 9.

* * * * *